(12) United States Patent
Villaseca et al.

(10) Patent No.: US 6,169,925 B1
(45) Date of Patent: Jan. 2, 2001

(54) TELEMETRY SYSTEM FOR IMPLANTABLE MEDICAL DEVICES

(75) Inventors: Eduardo H. Villaseca, Minneapolis; Garry L. Dublin, Maple Grove; Steven D. Goedeke, Forest Lake; Gregory J. Haubrich, Champlin, all of MN (US)

(73) Assignee: Medtronic, Inc., Minneapolis, MN (US)

( * ) Notice: Under 35 U.S.C. 154(b), the term of this patent shall be extended for 0 days.

(21) Appl. No.: 09/302,932

(22) Filed: Apr. 30, 1999

(51) Int. Cl.[7] .................................................. A61N 1/362
(52) U.S. Cl. .............................. 607/60; 607/30; 128/903
(58) Field of Search .................... 607/32, 60; 128/703

(56) References Cited

U.S. PATENT DOCUMENTS

| | | |
|---|---|---|
| 4,365,290 | 12/1982 | Nelms et al. . |
| 4,523,324 | 6/1985 | Marshall . |
| 4,542,532 | 9/1985 | McQuilkin . |
| 4,580,101 | 4/1986 | Lax . |
| 4,618,967 | 10/1986 | Vance et al. . |
| 5,113,869 | 5/1992 | Nappholz et al. . |
| 5,342,408 | 8/1994 | deCoriolis et al. . |
| 5,404,877 | 4/1995 | Nolan et al. . |
| 5,476,488 | 12/1995 | Morgan et al. . |
| 5,683,432 | 11/1997 | Goedeke et al. . |
| 5,693,076 | 12/1997 | Kaemmerer . |
| 5,720,770 | 2/1998 | Nappholz et al. . |
| 5,752,977 | 5/1998 | Grevious et al. . |
| 5,766,232 | 6/1998 | Grevious et al. . |
| 5,861,019 | 1/1999 | Sun et al. . |
| 6,009,350 | * 12/1999 | Renken ................................. 607/32 |

* cited by examiner

*Primary Examiner*—George R. Evanisko
(74) *Attorney, Agent, or Firm*—Reed A. Duthler; Harold R. Patton; Girma Wolde-Michael

(57) ABSTRACT

A device for use in communication with an implantable medical device. The device is provided with a spatial diversity antenna array mounted to a housing and an RF transceiver operating at defined frequency, coupled to the antenna alray. The antenna array comprises two antennas spaced a fraction of the wavelength of the defined frequency from one another, each antenna including two antenna elements mounted to the housing and located oithogonal to one another. Selection of which of the antennas is employed is accomplished by an device controller, responsive to the quality of the signals received by the antennas.

30 Claims, 8 Drawing Sheets

TELEMETRY SYSTEM FOR IMPLANTABLE MEDICAL DEVICES

BACKGROUND OF THE INVENTION

This invention relates generally to the implantable medical devices and more specifically to telemetry systems for allowing communication between implanted medical devices and external programmers or monitors.

In the context of implantable medical devices, it has become common to provide a communication link between the implanted device and an external programmer or monitor in order to allow for transmission of commands from the external device to the implanted device and to allow for transmission of stored information and/or sensed physiological parameters from the implanted device to the external programmer. Conventionally, communication between an implanted device and an external programmer has been accomplished by means of a telemetry system which includes a transceiver located within the implanted medical device and an external programmer or monitor, each having a radio transmitter/receiver and one or more antennas.

The implanted device typically includes an antenna located either within the hermetic device housing containing the circuitry, as disclosed in U.S. Pat. No. 4,542,532 issued to McQuilkn, in a plastic header or connector block used to interconnect the device to electrical leads as disclosed in U.S. Pat. No. 5,697,958 issued to Patrick et al. or mounted to the device housing as in U.S. Pat. No. 5,861,019 issued to Sun et al. and U.S. Pat. No. 5,720,770 issued to Nappholz et al., all incorporated herein in their entireties. The programmer or monitor typically includes or consists of a programming head containing an antenna, intended to be placed on the patient's body in close proximity to the implanted device. The programming head may be coupled to the external programmer or monitor by means of a cord, as disclosed in U.S. Pat. No. 5.766,232 issued to Grevious et al.

More recently it has been proposed to provide communication systems for implantable devices in which the programming head is done away with, and communication occurs directly between the programmer or monitor, which may be located some distance from the patient, and the implanted medical device. Such systems are disclosed in U.S. Pat. No. 5,404,877 issued to Nolan et al, and U.S. Pat. No. 5,113,869 issued to Nappholz. In the Nappholz patent, in particular, the use of an electrical lead as the antenna for broadcasting RF signals to the programmer or monitor which may be located some feet away from the patient is suggested.

SUMMARY OF THE INVENTION

The present invention is directed toward a telemetry system for an implantable device which, like the devices in the above cited Nolan and Nappholz patents allows for communication between an implanted device and an associated external programmer or monitor without the necessity of a programming head placed on the patient's body in close proximity to the implanted device. In conjunction with this invention, improved antenna configurations for the programmer and the implanted device are provided, optimized to allow for reliable communication between an implanted device and an external programmer or monitor antenna which may be spaced at least several feet from one another.

In preferred embodiments of the invention, the antenna of the implanted device takes the form of a monopole antenna located external to the hermetic enclosure of the implanted device, having a length tuned to function optimally at the radio frequencies chosen for use in the telemetry system. In a first embodiment of the invention, the antenna takes the form of a tab-loaded monopole, comprising a wire encased in an insulative material, extending from the connector block assembly of the device and coupled to the RF transceiver located within the device by means of a folded metal strip or tab located in the connector block, extending between the proximal end of the insulated wire and a feed-through coupled to the RF transceiver circuitry within the housing of the device. In particular, the folded metal strip may be fabricated of metal foil or metallized plastic film and may take the general form of an isosceles triangle provided with laterally extending tabs at its base. In this embodiment, the base of the triangle is coupled to the antenna while the opposite apex of the triangle is coupled to the feed-through and in turn to transceiver circuitry within the device housing. The length of the insulated wire is chosen to be optimized for the intended operational frequency range of the transceiver. In one preferred embodiment, the transceiver takes the form of a RF transceiver operating at about 400 megaHertz and the length of the insulated wire is approximately 12 centimeters. In particular, the insulated wire in this embodiment may be a stranded wire, insulated in a silicone rubber sleeve.

In a second embodiment, the antenna of the implanted device takes the form of a length of coaxial cable having a central or core wire coupled to a feedthrough, in turn coupled to transceiver circuitry within the device housing and having a coaxial shield extending over only a portion of the length of the cable. For example, in the context of an implanted device having a transceiver intended to operate in the vicinity of 400 megaHertz, the coaxial cable may extend for a length of approximately 12 centimeters from the point at which it is coupled to the feedthrough, of which length only the four centimeters closest to the feedthrough are provided with a coaxial shield. In particular, the antenna may be a length of coax type cable, having a metallic center conductor, a 3.1 plastic dielectric and a braided wire coaxial shield, stripped of its outer insulation and tripped of its coaxial shield over the eight centimeters most distant from the feedthrough. The four centimeters over which the shield extends may conveniently be located in the connector block of the device, with the remaining eight centimeters either extending freely outward from the connector block or mounted to the device housing and encased in an insulating material.

In either of the two embodiments described above, the antenna may be manufactured as an integral part of implanted device or, that portion of the antenna extending external to the connector block may be manufactured as a separate piece part, coupled to the portion of the antenna within the connector block by means of a standard electrical connector. In this context, the portion of the antenna extending from the connector block may be included as a portion of an implantable stimulation lead, also inserted into the connector block. In a preferred embodiment, the portion of the antenna located external to the connector block is mechanically coupled at its distal end to the stimulation lead.

A programmer or monitor according to the invention is provided with a spatial diversity antenna array in order to facilitate reception of signals from the implanted device and transmission of signals to the implanted device, within a wide area surrounding the monitor or programmer. One appropriate embodiment of an antenna for the programmer or monitor takes the form of two antennas, each comprising two conductive plates or strips mounted orthogonally to one another on exterior or interior surfaces of a housing which may be the programmer or monitor housing. In this embodiment, the portion of the housing to which the antennas are mounted is fabricated of a non-conductive material such as plastic. The two metallic plates of each antenna may be mounted adjacent opposing corners edges of the housing. For example, in the context of programmers or monitors provided with an LCD or CRT display, the antennas may be mounted adjacent opposite upper corners of the housing enclosing the display. In such an embodiment, each of the two antennas would include a plate mounted to the Lipper surface of the display housing and a plate mounted to an adjacent side surface of the display housing.

In each of the two antennas, the two plates or strips are coupled to an RF feed cable by means of a 180° splitter and tuned circuit. Selection of which of the two antennas is employed to transmit or receive signals from the implanted device is made by means of control circuitry within the programmer or transmitter. Selection may be made based on the magnitude of the signal received by the programmer or monitor from the implanted device or may be made in response to the establishment of a robust communication link between the implanted device and the monitor or programmer.

In a second embodiment of a programmer or monitor according to the present invention, a spatial diversity antenna array is provided which comprises two antennas, each including a pair of tuned stub antenna elements mounted orthogonal to one another and located adjacent opposite corner edges of a housing which may be a portion of the programmer or monitor housing, in a fashion analogous to the plate or strip antennas described previously. In this embodiment, the portion of the housing to which the stub antennas are mounted is conductive, rather than insulative. For example, the portion of the device carrying the antennas may take the form of a generally rectangular, box-like enclosure with antennas located adjacent opposite edge corners of the enclosure such that each of the antennas includes a stub antenna extending upwards from an upward surface of the enclosure and a stub antenna extending laterally outward from an adjacent side surface of the enclosure, preferably oriented 90° from the antenna extending from the upper surface of the enclosure. Like the plate antennas described above, the two adjacent stub antenna elements are coupled to a 180° power splitter and tuned circuit, each of which is in turn coupled to a selector switch to allow selection between either of the two antennas. As discussed in conjunction with the plate antenna array described above, selection of which of the two antennas is employed may be accomplished by either a measurement of received signal strength or verification of accurate data transmission.

In conjunction with both embodiments of the antennas arrays for use in conjunction with the programmer or monitor, the antenna pairs are preferably spaced by a fraction of a wavelength of the center frequency of the transceivers employed in the implanted device and the programmer/monitor. For example, in conjunction with some embodiments intended for use in conjunction with transmitters and receivers operating at approximately 400 megaHertz, the two antennas may be spaced approximately 11.5 to 12.5 inches from one another.

BRIEF DESCRIPTION OF THE DRAWINGS

FIG. 1b illustrates the configuration of an antenna plate as employed in the programmer or monitor of FIG. 1a.

FIG. 2b is an illustration of a tuned stub antenna element as employed in the programmer or monitor of FIG. 2a.

FIG. 3 is a functional diagram illustrating the interconnection of the antenna array RF circuitry and other functional components of the programmer or monitor illustrated in FIG. 1a.

FIG. 4 is a drawing illustrating the corresponding interconnection of the antenna array of FIG. 2a with the circuitry of the programmer or monitor of FIG. 2a.

FIG. 6b illustrates the configuration of the metal tab portion of the antenna of the device of FIG. 6a.

DETAILED DESCRIPTION OF THE DRAWINGS

Figure 1A:
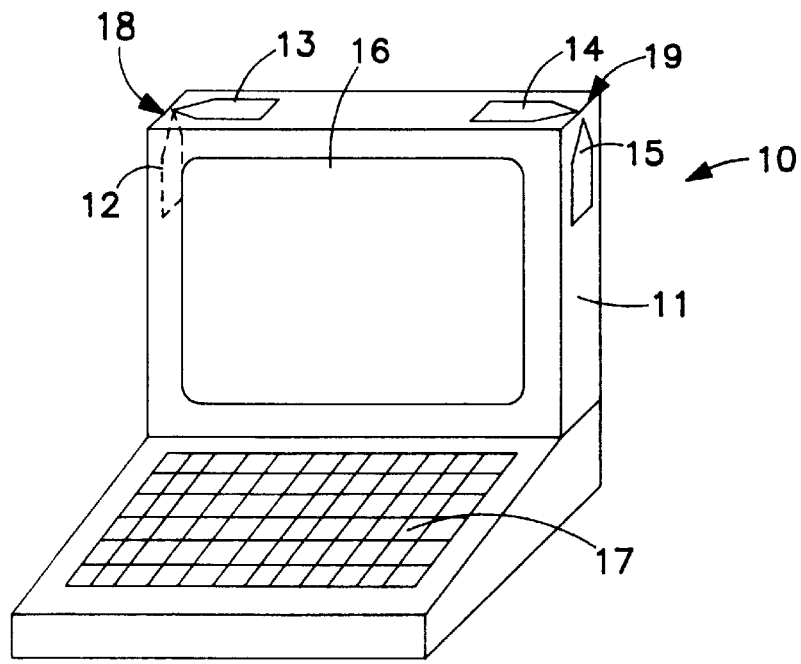
FIG. 1a is a perspective view of a programmer or monitor provided with a first antenna array according to the present invention.

FIG. 1a is a perspective drawing of a programmer or monitor 10 appropriate for use in practicing the present invention. The monitor is provided with a display 16 which may take the form of an LCD display or a CRT and a keyboard 17 which allows the physician to enter commands. The antenna array of the programmer or monitor 10 includes two antennas, each antenna comprising two orthogonally located antenna elements, illustrated in FIG. 1 as antenna elements 13, 14 and 15. A fourth antenna element 12 is indicated in broken outline. In this embodiment, the monitor housing is made of non-conductive material and the antenna elements are located either on the exterior or interior surface of the housing, as is convenient.

The two elements of each antenna take the form of metal strips or plates located relative to one another such that the plates or strips define planes which are generally orthogonal to one another. For example, elements 14 and 15 are located on internal or external surfaces adjacent a comer edge 19, of the monitor housing 11 and elements 12 and 13 are located on internal or external surfaces adjacent a an opposite corner edge 18 of the monitor housing 11. The two antennas are preferably oriented so that each plate or strip of an antenna defines a plane which is parallel to or coplanar with the plane defined by a corresponding plate or strip of the other antenna. For example, plates or strips 13 and 14 are generally coplanar and plates or strips 12 and 15 are generally parallel. The two antennas are preferably separated by a fraction of the wavelength of the center frequency employed by the transceivers in the programmer/monitor and implanted device. In the context of a telemetry system operating in the vicinity of 400 megaHertz, for example, the spacing between antenna elements 13 and 14 may be, for example, about 7 inches. The orientation of the antenna elements provides for spatial diversity, facilitating the ability to receive transmissions from the implanted device when located at any number of locations in the general vicinity of the programmer/monitor, providing for greater flexibility in use of the telemetry system. Although not illustrated in FIG. 1, in each antenna, the two elements are coupled to one another by means of a 180° power splitter/tuned circuit, and the programmer/monitor is provided with circuitry therein for selecting between the two antennas, based on signal strength and/or verification of accurate transmission from the implanted device.

Figure 1B:
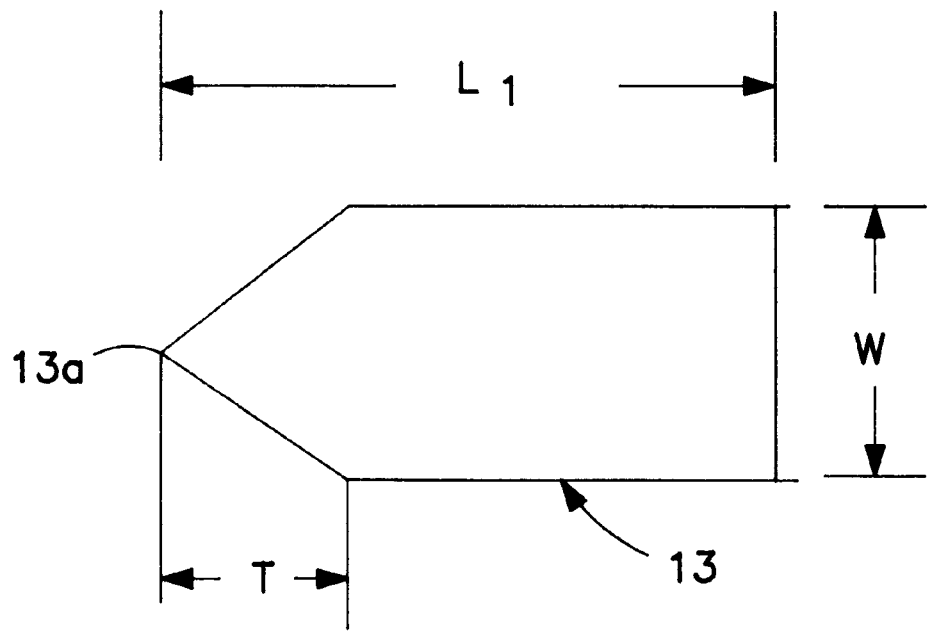

FIG. 1b illustrates an exemplary antenna element appropriate for use in a programmer or monitor as illustrated in FIG. 1. The antenna element 13 as illustrated may be fabricated from a 0.005" thick sheet of copper or other highly conductive metal mounted to an inner or outer surface of the non-conductive housing of the programmer or monitor. Alternatively, the antenna element may be copied by depositing a similarly configured coating of copper or other highly conductive metal on an inner or outer surface of the non-conductive housing of the programmer or monitor. In the particular embodiment illustrated, the antenna element takes the form of a strip having a length L, of approximately 2" and a width W of approximately 1.25". One end of the strip is tapered over a length T of approximately 1.8" to a point 13a. The antenna element is preferably coupled to the power splitter/tuned circuit within the housing of the programmer or monitor by means of a feed line attached adjacent point 13a.

Figure 2A:
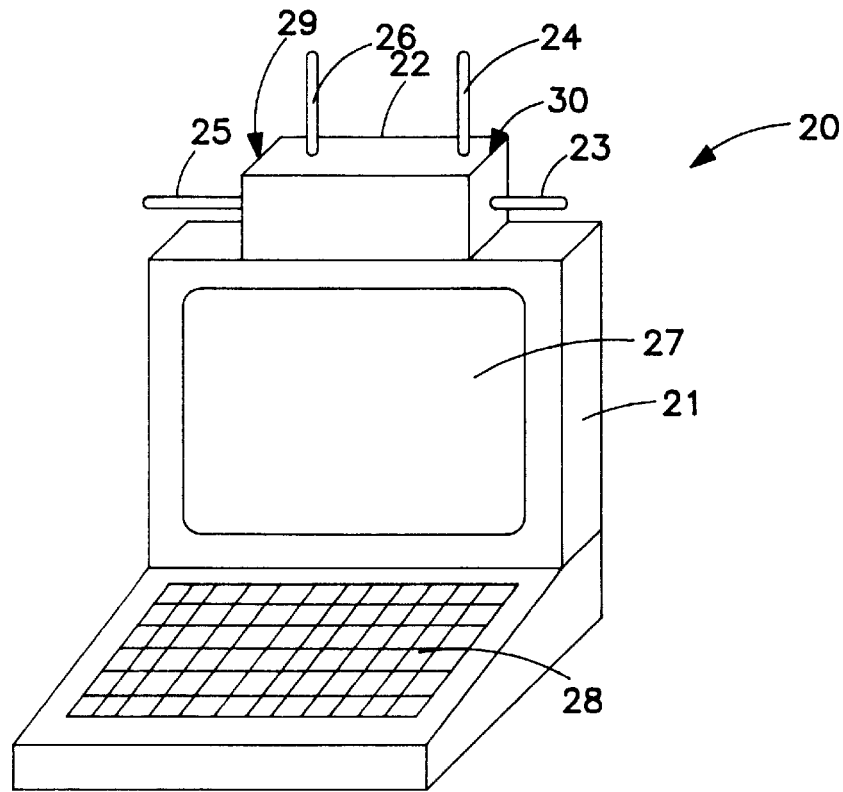
FIG. 2a is a perspective view of a programmer or monitor provided with a second embodiment of an antenna array according to the present invention.

FIG. 2a is a perspective drawing of an alternative embodiment of a programmer or monitor appropriate for use in conjunction with an implanted device according to the present invention. In this embodiment, the programmer or monitor is similarly provided with a display 27 located in the display housing 21 and with a keyboard for entry of commands by the physician. In this embodiment, however, the antennas are mounted to a conductive, generally rectangular housing 22. In this embodiment, two antennas are provided, each antenna comprising two orthogonally oriented tuned stub antenna elements. The first antenna includes antenna elements 23 and 24 which are mounted so that their longitudinal axes are located orthogonally to one another adjacent an upper edge 30 of the housing 22. The second antenna comprises antenna elements 25 and 26 which are likewise mounted so that their longitudinal axes are located are orthogonal to one another adjacent in upper edge 29 of the metallic housing 22. Antenna elements 23, 24, 25 and 26 may be coiled stub antennas elements, having lengths optimized for use in receiving the center frequency of the transceivers employed by the programmer or monitor and the implanted device.

The antenna of FIG. 2a array employs two horizontally directed stub antenna elements 23 and 25 which have their axes generally parallel or co-linear with one another and two vertically directed stub antenna elements 24 and 26 which have their axes parallel to one another but perpendicular to the horizontally directed stub antenna elements 23 and 25. preferably the axes of the stub antenna elements of each of the antennas are coplanar and the axes of all stub antenna elements in both antennas may likewise be coplanar. The antennas are preferably spaced a fraction of the center frequency wavelength from one another. For example, in the embodiment illustrated in FIG. 2, the stub antenna elements 24 and 26 may be spaced approximately 12 inches from one another. Although not visible in this drawing, it should be understood that the two elements of each antenna are coupled to one another by means of a 180° power splitter/ tuned circuit, located within housing 22. As in the case of the programmer or monitor illustrated in FIG. 1a, the device includes circuitry for switching between the two antennas as a function of either the signal strength of the signal received from the signal received from the associated implanted device or as a function of verification of accurate data transmission.

Figure 2B:
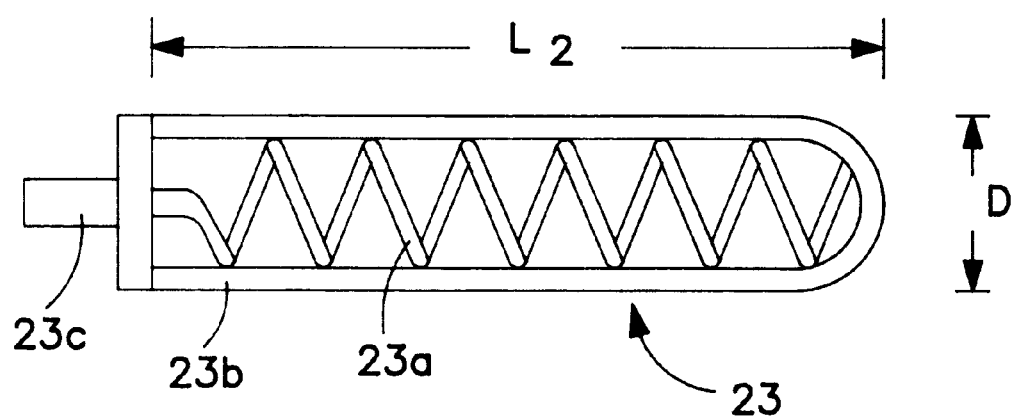

FIG. 2b illustrates the configuration of a stub antenna element appropriate for use with a programmer or monitor as illustrated in FIG. 2a. For example, in the case of a telemetry system operating the range of 400 megaHertz, the stub antenna element 23 may be a coil of number 12 wire 23a having a diameter D of ¼ to ⅜", and a length $L_2$ of about 2", covered by a sheath 23b of rubberized plastic and mounted to a connector base 23c which allows the antenna element to be mounted to and insulated from the conductive housing of the programmer or monitor.

Figure 3:
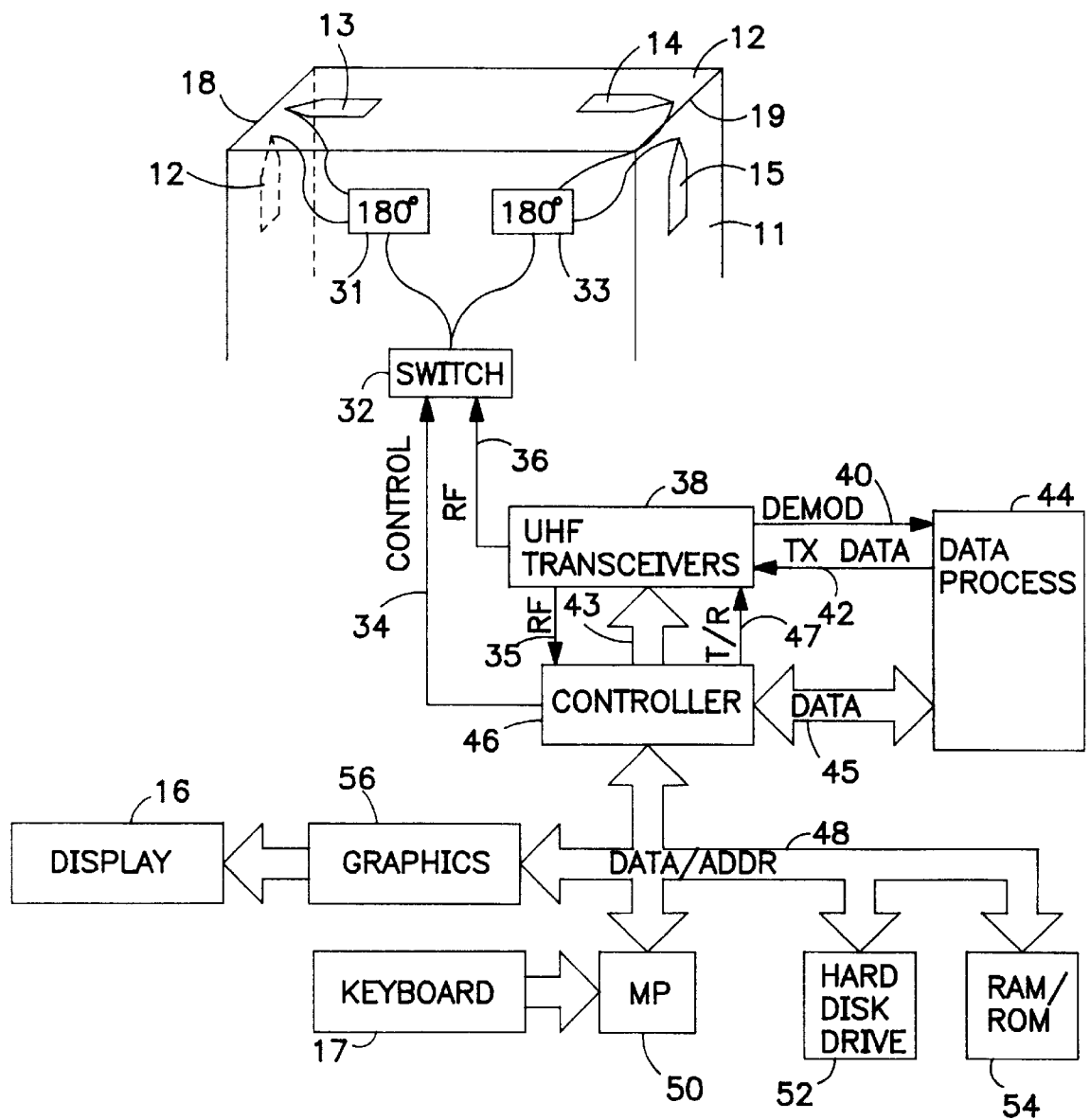

FIG. 3 is a diagram illustrating the interconnection of the antenna array of the programmer or monitor of FIG. 1a with the circuitry and other functional components included therein. In this view, the outline of the display housing 11 is illustrated, showing the relative location of antenna elements 12, 13, 14 and 15. The tapered end portions of plates or strips 12 and 13 are coupled by feed wires to a 180° power splitter/tuned circuit 31 which is in turn coupled to antenna selection switch 32. Similarly, the tapered end portions of plates or strips 14 and 15 of the second antenna are coupled to a second 180° power splitter/tuned circuit 33 which is also coupled to antenna selector switch 32. The controller circuitry 46 of the programmer selects which of the two antennas is employed by means of control line 34. RF signals are carried between the antenna switch 32 and UHF transceiver 38 via RF line 36.

The circuitry within the programmer or monitor includes a microprocessor 50 which controls the operation of the device as a function of programming stored in RAM/ROM 54 and/or hard disk drive 52, both of which are coupled to the microprocessor via data/address bus 48. Commands from the physician are provided to the microprocessor via keyboard 17 and/or any additional control buttons (or if the display is touch sensitive from the display as well). Information regarding the operation of the programmer or monitor and information received from the associated implanted device are displayed on display 16, under control of graphics circuitry 56. The graphics circuitry, microprocessor, hard disk drive, RAM/ROM circuitry, keyboard and display may all correspond to corresponding components of personal computers and/or prior art programmers and monitors.

Operation of the telemetry system is controlled by controller circuit 46 which operates under control of microprocessor 50. UHF transceiver 38 is a multi-frequency transceiver, preferably a transceiver capable of operating in a number of frequency bands, in which data is encoded by frequency shift from a defined center frequency. Controller 46 via control bus 43 defines the operational frequency of the transceiver 38, and by means of transmit/receive line. 47 configures the transceiver to either transmit RF signals to the antennas or receive RF signals from the antennas. Controller 46 also provides the data to be telemetered to the implanted device to data processing circuitry 44 and receives decoded received data from the implanted device from data processing circuit 44, also via data bus 45. Data provided by controller 46 to data processing circuitry 44 is converted therein from parallel to serial format and provided serially to UHF transceiver 38 on TX data line 42. Correspondingly, data received by UHF transceiver 38 is provided in serial format on DEMOD line 40 to data processing circuitry 44, and is converted therein to parallel format and provided to the microprocessor 50 via controller circuitry 46. Controller 46 is also capable of monitoring the amplitude of the signal received by the currently active antenna via RF line 35 from UHF transceiver 38 in order to allow for selection between the two antennas as described above. In operation, during receipt of transmissions from the associated implanted device, the controller 46 may select which of the two antennas is employed as a function of the amplitude of the received RF signal as indicated on RF line 35. Alternatively, the controller may verify the integrity of the data received from data processing circuitry 44 via data line 45, and switch between antennas in the event that the received data has greater than a defined number of errors per transmission.

Figure 4:
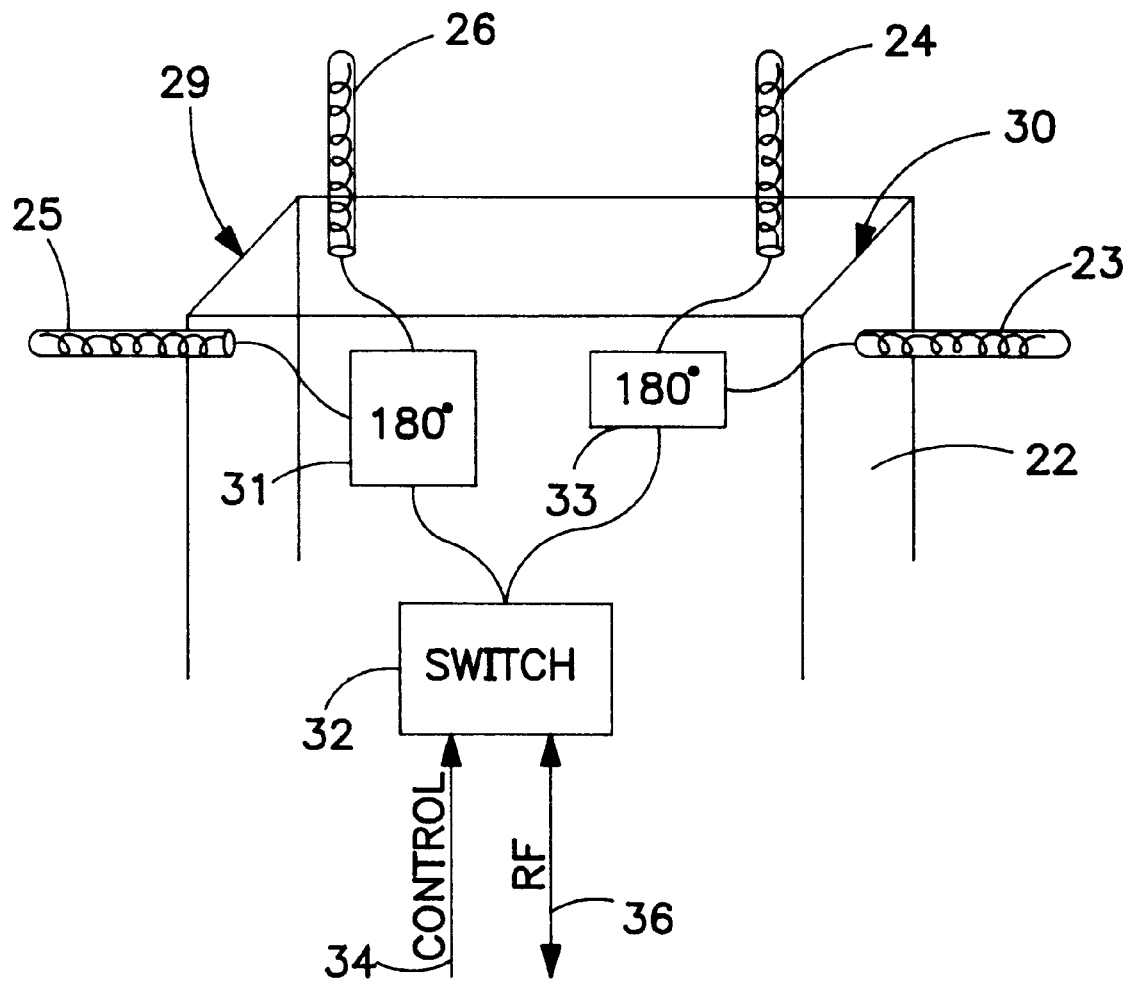

FIG. 4 is a figure illustrating the interconnection of the stub antenna elements 23, 24, 25 and 26 of FIG. 2a with corresponding circuitry within the programmer or monitor 20 of FIG. 2a. As illustrated, the first antenna includes stub antenna elements 25 and 26, located adjacent the upper edge 29 of metallic enclosure 22. Stub antenna elements 25 and 26 are coupled to a 180° power splitter/tuned circuit 31 which corresponds to the identically labeled circuit in FIG. 3. Similarly, the stub antenna elements 23 and 24 of the second antenna, located adjacent tipper edge 30 of enclosure 22 are also coupled to a 180° splitter/tuned circuit, which also corresponds to the identically numbered component in FIG. 3. The 180° power splitter/tuned circuits 31 and 33 are correspondingly coupled to an antenna selector switch as corresponding to that illustrated in FIG. 3 which is coupled to the circuitry within the programmer/monitor via RF line 36 and control line 44 in the same fashion as described in conjunction with FIG. 3.

While each of the spatial diversity antenna arrays in FIGS. 1–4 discussed above is mounted to a portion of the programmer or monitor housing which also houses the display, it is of course also possible to mount the antenna arrays to another portion of the programmer or monitor housing or to a separate housing, coupled to the device housing by means of a cable. For example, the metal enclosure 22 of FIG. 4 might be mounted to a portion of the programmer other than the display housing 21 or might be coupled to the programmer by means of a cable, allowing the enclosure 22 to be placed adjacent the programmer or at a distance from the programmer as is convenient, allowing for optimal antenna location independent of the programmer. Similarly, the antenna array of FIG. 3 might also be located on a different portion of the programmer housing or located on a separate, non-conductive housing coupled to the programmer by means of a cable. In either case, if the antenna array is located in or on a housing separated from the programmer, the 180° power splitter/tuned circuits preferably would also be located in the separate housing, which may optionally also include the antenna selector switch.

Figure 5:
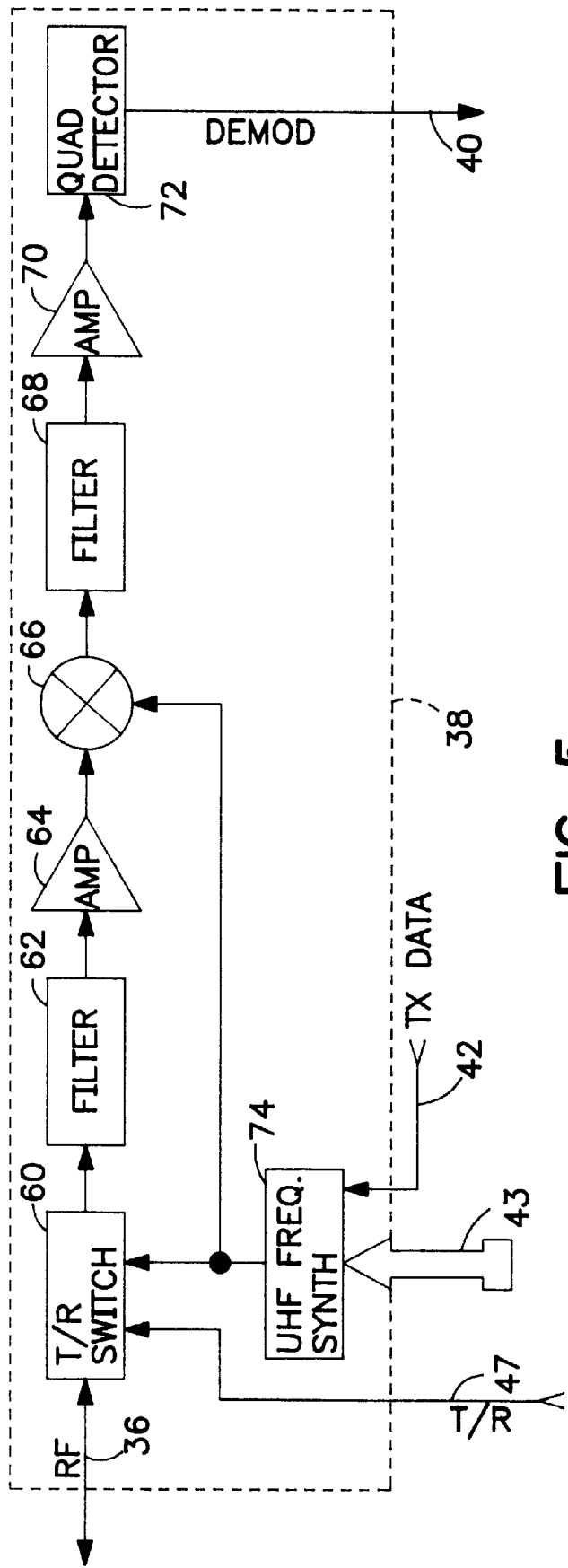
FIG. 5 illustrates an exemplary type of RF transceiver appropriate for use in conjunction with the programmer or monitors of FIGS. 1–4 above and for use in conjunction with an implantable device embodying the present invention.

FIG. 5 is a block functional diagram of one type of transceiver appropriate for use in conjunction with the present invention in both the implanted device and the associated programmer. As illustrated, the transceiver is shown as it would be interconnected to the circuitry of the programmer or monitor. However, the description of its operation below also applies to the transceiver as employed in the implanted device. Other transceiver types corresponding, for example to transceivers employed in prior art implantable devices and associated programmers may of course be substituted, with corresponding dimensional changes to the antennas as disclosed herein to optimize their performance for the frequencies employed by the transceivers.

Examples of alternative transceivers are described in U.S. Pat. No. 5,342,408, issued to DeCoriolis ct al., U.S. Pat. No. 5,476,488, issued to Morgan et al., U.S. Pat. No. 5,683,432, issued to Goedeke et al., U.S. Pat. No. 4,365,290, issued to Nelms et al. and U.S. Pat. No. 5,693,076, issued to Kaemmerer or U.S. Pat. No. 5,752,977, issued to Grevious et al., all incorporated herein by reference in their entireties, or as disclosed in any of the above-cited prior patents related to programmers for use with implantable devices.

In particular, the transceiver 38 may be configured to operate employing center frequencies in the vicinity of 400 megaHertz. The receiver includes a UHF frequency synthesizer 74 which operates under control of control bus 43 to define a center frequency and data frequencies spaced above and below the center frequency. A number of center frequencies and associated data frequencies may be defined to provide for multi-channel operation. Control of the transceiver to operate as a transmitter or receiver is accomplished through the transmit/receive control line 47 which causes transmit/receive switch 60 to couple RF line 36 (coupled to the antenna array) to either the frequency synthesizer 74 or to mixer 66 via one or more filtration and amplification stages 62 and 64. While operating as a receiver, the UHF frequency synthesizer applies the center frequency to the mixer 66 and thereafter to quadrature detection circuitry 72 via one or more filtration and amplification stages 68 and 70. The demodulated quadrature signal on line 40 is passed through to the data processing circuitry 44 where it is converted from a serial to a parallel format and thereafter provided to the microprocessor 50 via control circuitry 46 and data/address bus 48 (FIG. 3).

During transmission, the transmit/receive switch 68 couples the RF line 36 (in turn coupled to the antenna array) to the output of the UHF frequency synthesizer 74 which outputs a frequency shifted above or below the center frequency as a function of the logic value of the serially applied data on TX data line 42. The associated implanted device correspondingly has a similar UHF transceiver operating in an analogous fashion to receive the RF signals from the programmer or monitor and to transmit RF signals to the programmer/monitor.

Figure 6A:
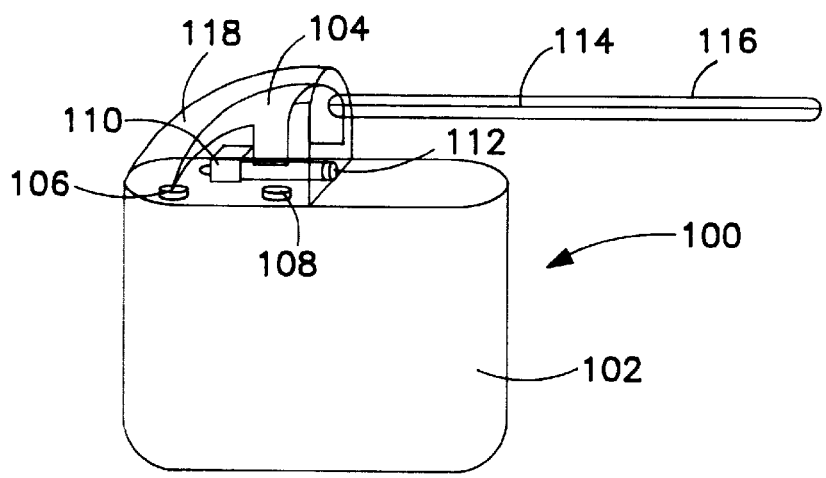
FIG. 6a is a plan view of an implantable device according to the present invention employing a first embodiment of an antenna.

FIG. 6a is a perspective view of a first embodiment of an implanted device 100 embodying the present invention. The device includes a hermetic enclosure 102 which includes a battery and electronic circuitry, including an RF transceiver as described above. Mounted to the enclosure 102 is a header or connector block 118 which is preferably fabricated of a plastic such as epoxy. As illustrated, the plastic is transparent, however, an opaque plastic or other insulative material may also be substituted. As illustrated, the device includes a connector bore 112 which is intended to receive the electrical connector of an associated electrical lead, such as a cardiac pacing lead, a cardiac monitoring lead, a cardioversion/defibrillation lead, or a lead coupled to a physiologic sensor such as an oxygen sensor, pressure sensor, or the like. The lead is coupled to the internal circuitry within the enclosure 104 by means of one or more electrical connectors 110, each coupled to an associated feedthrough 108 and thereby coupled to the circuitry within enclosure 102. The portion of the antenna external to the connector block may take the form of a wire 114 surrounded by an insulative coating 116. The wire may take the form of a stranded conductor, for example a 0.020" diameter stranded wire surrounded by silicone rubber insulation 116. The length of wire 114 is chosen to be optimized for use in conjunction with the center frequency of the UHF transceiver within the device 100. In the context of a device operating in the vicinity of 400 megaHertz, for example, the length of conductor 114 may be approximately 8 centimeters. Mounted within connector block 118 is a metallic antenna loading tab 104 which takes the general form of an isosceles triangle having laterally extending tabs at its base and coupled at its apex to a feedthrough 106 which is in turn coupled to the UHF transceiver within the device 100. Wire 114 is coupled to the base of the loading tab 104, as illustrated in more detail in FIG. 6b.

Figure 6B:
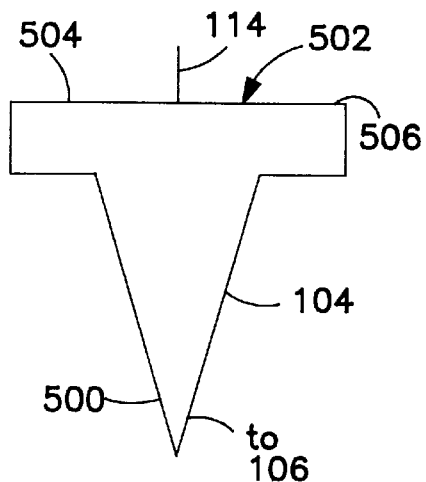

FIG. 6b illustrates one preferred configuration for the antenna loading tab 104. As illustrated, the tab generally takes the form of an isosceles triangle having an apex 500 which is coupled to the feedthrough 106 and thereby to the UHF transceiver within the housing and a base 502 which is coupled to the stranded wire 114 of the antenna. The base portion of the tab is provided with two lateral extensions 504 and 506. The tab may be fabricated of a gold plated plastic sheet approximately 0.020" in thickness, and the length of the tab from the apex 500 to the base 502 may be approximately 1.6. The tab may alternatively be deposited on an external surface of the connector block and covered with a plastic or silicone rubber coating. The antenna configuration illustrated in FIGS. 6a and 6b is particularly desirable in the context of an implanted device employing a UHF transceiver. The antenna so provided is a broad band high efficiency antenna, in which the tab 104 functions as a sub-wavelength radiating element and in which the length of the wire 114 is chosen to provide optimal performance for the particular frequency bands employed by the transceiver.

Figure 7:
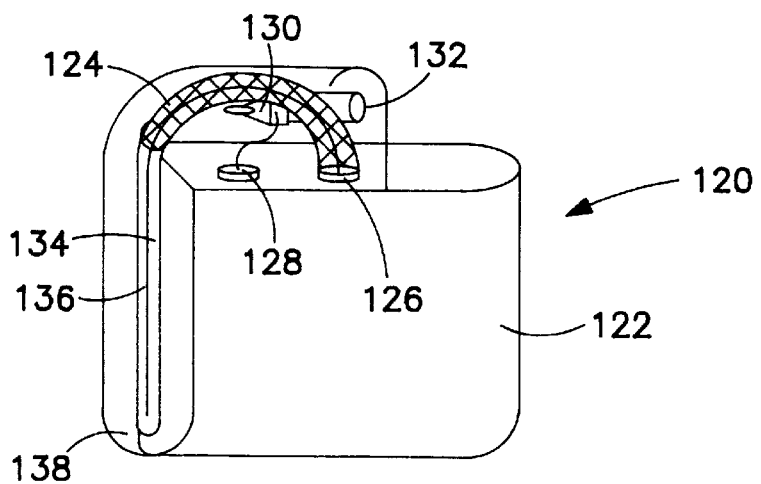
FIG. 7 illustrates an implantable device 120 according to the present invention employing a second embodiment of an antenna.

FIG. 7 illustrates an implantable device 120 employing an alternative antenna embodiment. Like the device of FIG. 6a, the device includes an enclosure 122 which contains a battery and associated electronic circuitry including a UHF transceiver as discussed above. Mounted to the enclosure is a connector block 138 which in this case is a generally "L" shaped molded plastic component extending over two adjacent edge surfaces of the enclosure 122. Like the connector block 118 of FIG. 6a, connector block 138 is also provided with a connector bore 132 and one or more electrical connectors 130 coupled to electronic circuitry within the enclosure 122 by means of one or more feedthroughs 128. In this embodiment, the antenna takes the form of a length of coaxial cable having its center conductor 134 coupled to a feedthrough 126 which is in turn coupled to the transceiver within the enclosure 122 and having a braided shield 124 coupled to the device enclosure 122, which is typically fabricated of a conductive material such as stainless steel or titanium. The braided shield 124 is electrically coupled to the enclosure 122 and extends over only a portion of the length of the antenna, with the remainder of the antenna consisting of the unshielded center conductor 134 surrounded by diametric 136. For example, the antenna may take the form of a shielded RF type coax cable with its outer insulation removed, having a 0.020" diameter center conductor fabricated of stranded wire, a cable dielectric of 3.1 plastic and a braided wire outer shield. The antenna may be approximately 12 centimeters in length, and the braided shield 124 may extend only 4 centimeters from the point of connection of the cable to feedthrough 126. The entire antenna in this embodiment is molded into connector block 138, avoiding any inconvenience associated with a projecting antenna as in FIG. 6a.

Figure 8:
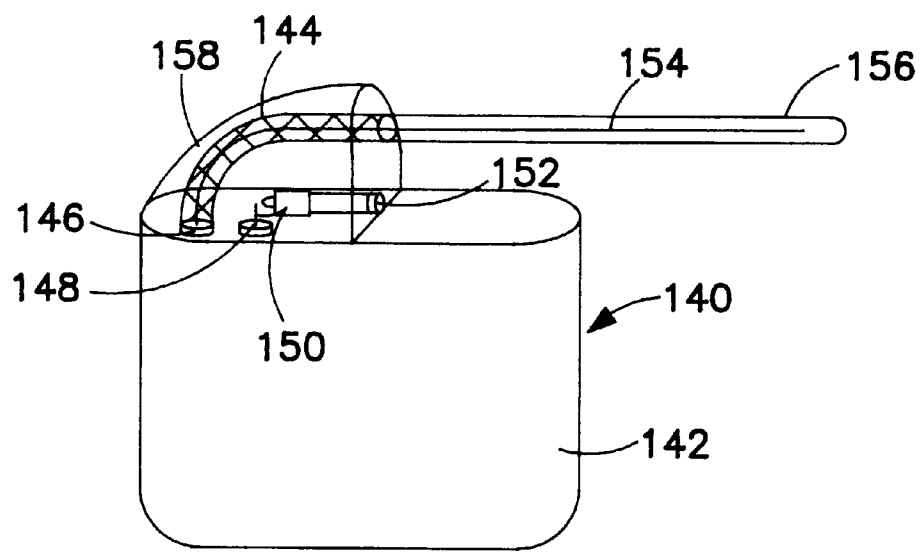
FIG. 8 is a plan view of an implantable device according to the present invention employing a third embodiment of an antenna.

FIG. 8 illustrates yet another alternative embodiment of an implantable device 140 employing the present invention. Like the devices of FIGS. 6a and 7, the device is provided with a hermetic enclosure 142 which contains a battery and associated electronic circuitry including a UHF transceiver. A connector block 154 is mounted to the enclosure and carries a connector bore 152 and one or more associated electrical connectors 150 each coupled to an associated feedthrough 148 as described above. In this embodiment, like the embodiment of FIG. 7, the antenna takes the form of a length of coaxial cable, coupled to a feedthrough 146 which is in turn coupled to the transceiver within the device 142 and having a braided shield 144 coupled to the conductive device enclosure 142.

In this embodiment, like the embodiment of FIG. 7, the braided shield 144 extends over only a portion of the antenna. For example, as discussed above in conjunction with FIG. 7, the 4 centimeters of the cable extending from the feedthrough 106 may be covered by braided shield 144, with the center connector 154 unshielded over the remainder of the length of the antenna which may total, for example, 12 centimeters. In this embodiment, the unshielded portion of the center conductor 154 and the associated dielectric 156 of the cable extend outward from the connector block 152 to provide a configuration which is similar externally to that illustrated in conjunction with that of FIG. 6a. The antennas of FIGS. 7 and 8, like the antenna of FIGS. 6a and 6b are particularly desirable for use as antennas in conjunction with implanted devices employing UHF transceivers, as they provide a broad band, high efficiency antenna for transmission and reception of UHF radio signals.

Figure 9:
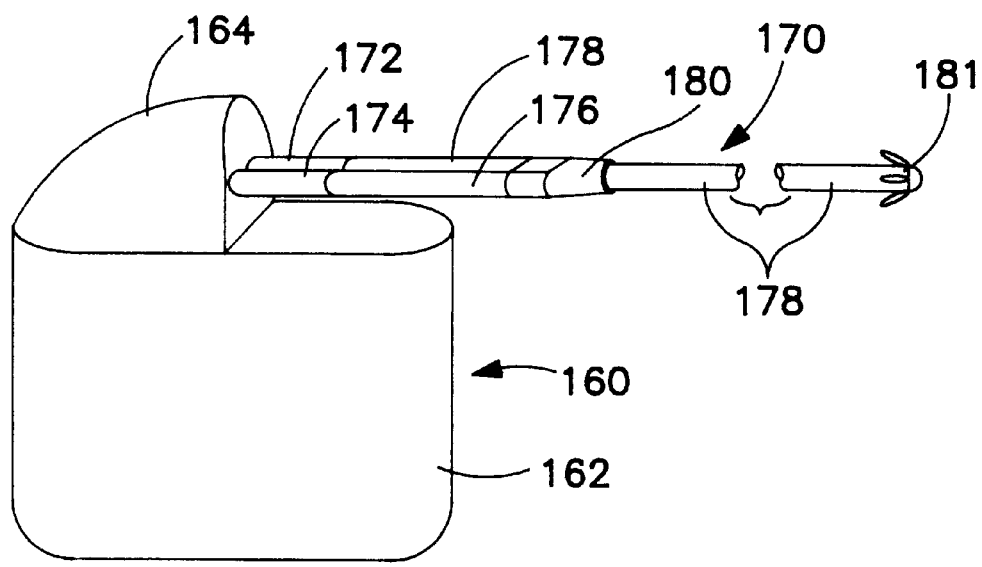
FIG. 9 is a plan view of an implantable device illustrating how antennas generally corresponding to those of FIGS. 6 and 8 may be combined with an electrode lead for use in an implantable device according to e present invention.

FIG. 9 is a perspective drawing of an implantable device 160 in which the portion of the antenna which extends outward from the connector block, for example, as illustrated in FIGS. 6 and 8, is configured to be part of an associated electrical lead 170. In this embodiment, the electrical lead is provided with a first electrical connector 172 which carries a conductor extending through an insulative lead body 178 to a stimulation/sensing electrode 180, for example, as might be employed if the implanted device takes the form of a cardiac pacemaker. The portion of the antenna 176 which extends exterior to connector block 164 is coupled to the lead body 178 by means of a molded plastic collar 180 and is provided with a second connector assembly 174 which is inserted into a second connector bore within connector block 164 which couples the exposed portion 176 of the antenna to the remainder of the antenna located within the connector block. For example, in the context of an antenna generally as illustrated in FIGS. 6a and 6b, the exposed portion of the antenna 176 may take the form of a stranded conductor in a silicone rubber insulation, and connector 174 may serve, in conjunction with an internal connector block would couple the exposed portion 176 of the antenna to the tab located within header 164. Correspondingly, in a device having an antenna generally as illustrated in FIG. 8, the exposed portion 176 of the antenna may take the form of the center conductor and dielectric of a coaxial cable, coupled to a short length of shielded coaxial cable within connector block 164 by means of convector 174.

Figure 10:
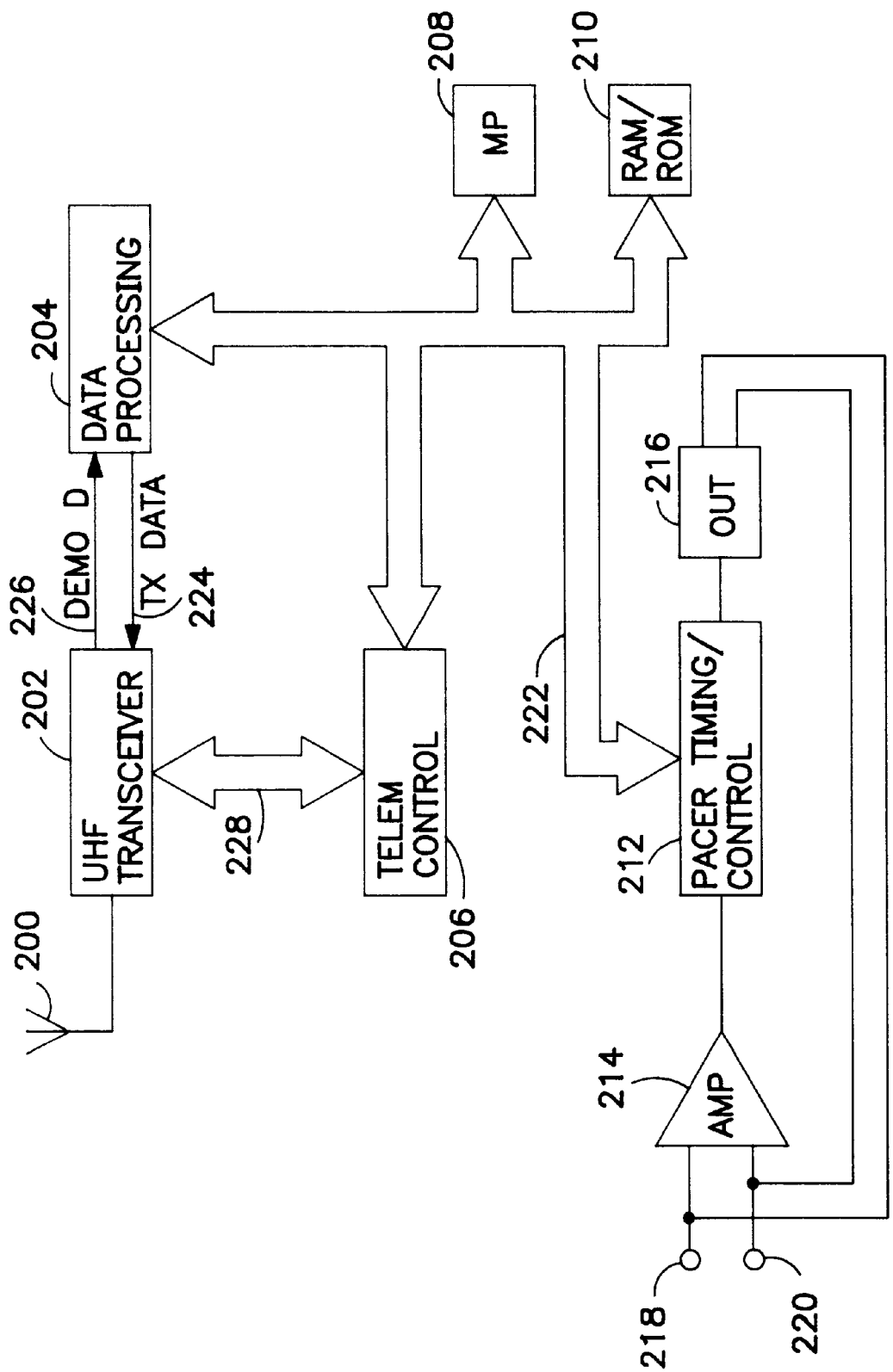
FIG. 10 is a functional block diagram of an implantable device according to the present invention.

FIG. 10 is block functional diagram of an implantable device appropriate for use in practicing the present invention. In this case, the device takes the form of an implantable cardiac pacemaker, which operates under control of microprocessor 208 under control of programming stored in RAM/ROM circuitry 210. Basic timing and operational functions of the pacemaker are provided by pacer/timing control circuitry 212, which defines the various escape intervals, pulse widths, sensing intervals and the like associated with operation of a cardiac pacemaker. Selection of intervals in operative modes is accomplished by microprocessor 208 via data/address bus 222. As illustrated, the device is provided with an input amplifier 214 which senses cardiac depolarizations via electrodes 218 and 220. For example, electrodes 218 and 220 may be located on an electrical lead associated with the device and inserted into a connector receptacle of the header coupled to the device enclosure, as illustrated in FIGS. 6 through 9, above. An output pulse generator 216 is provided for delivering cardiac pacing pulses to electrodes 218 and 220 according to any of the standard cardiac pacing modes. The illustrated embodiment of the implantable device as a cardiac pacemaker is purely exemplary, and it should be understood that the implantable device may of course take the form of an implantable naive stimulator, implantable heart monitor, implantable drug pump or any other implantable electronic device which employs a telemetry system to communicate between the implanted device and an associated external programmer or monitor.

The telemetry circuitry of the device corresponds generally to that discussed above in conjunction with FIG. 3 in the context of the associated external programmer or monitor. The antenna 200 which may take the form of any of the antennas illustrated in FIGS. 6 through 9 is coupled to a UHF transceiver 202 which may correspond to the UHF transceiver 38 illustrated in FIGS. 3 and 5 described above. Alternatively, the transceiver 38 may take the form of a zero IF or direct conversion transceiver of the general type described in U.S. Pat. No. 4,523,324 issued to Marshall et al., U.S. Pat. No. 4,618,967 issued to Vance et al and U.S. Pat. No. 4,580,101 issued to Lax et al., all incorporated herein by reference in their entireties. The transceiver in such embodiments may correspond generally to zero IF direct conversion FSK paging receivers intended to operate in the UHF band.

Like the circuitry within the programmer, operation of the transceiver is controlled via control bus 228 by telemetry control circuitry 206 which may correspond generally to control circuitry 46 of FIG. 3. Demodulated data from UHF transceiver 202 is provided via DEMOD line 226 to data processing circuitry 204 which converts the data from serial format to parallel format and provides it to microprocessor 208 via data/address bus 222. Data to be transmitted is converted from parallel format to serial format and provided to the transceiver via TX data line 224, in a fashion analogous to that discussed above in conjunction with FIG. 3 in the context of the external programmer or monitor.

In conjunction with the above specification, we claim:

1. An external device for use in communication with an implantable medical device, comprising:
   a device controller;
   a housing;
   an antenna array mounted to the housing;
   an RF transceiver operating at defined frequency, coupled to the antenna array;
   means for encoding signals to be transmitted to the implantable device, coupled to an input of the transceiver;
   means for decoding signals received from the implantable device, coupled to an output of the transceiver; and
   means for displaying the decoded signals received from the implantable device;
   wherein the antenna array comprises two antennas spaced a fraction of the wavelength of the defined frequency from one another, each antenna comprising two antenna elements mounted to the housing and located orthogonal to one another; and
   wherein the device controller includes means for selecting which of the two antennas is coupled to the transceiver.

2. A device according to claim 1 wherein a portion of the housing is conductive and each antenna comprises two tuned stub antenna elements having major axes orthogonal to one another, mounted to and extending from the conductive portion of the housing.

3. A device according to claim 2 wherein the major axis of each tuned stub element in one of the antennas is generally coplanar to the major axis of one of the stub elements in the other of the antennas.

4. A device according to claim 2 wherein the major axis of each tuned stub element in one of the antennas is generally parallel to the major axis of one of the stub elements in the other of the antennas.

5. A device according to claim 1 wherein at least a portion of the housing is non-conductive and each antenna comprises two generally planar conductive antenna elements mounted to the non-conductive portion of the housing and located generally along two mutually orthogonal planes.

6. A device according to claim 5 wherein the antenna elements are mounted along surfaces of the housing.

7. A device according to claim 5 wherein the antenna elements are metal strips or sheets adhered to surfaces of the housing.

8. A device according to any of claims 1–7 wherein the two antenna elements are coupled to one another by means of a 180 degree splitter.

9. A device according to claim 8 wherein the transceiver is a UHF transceiver.

10. A device according to any of claims 1–7 wherein the transceiver is a UHF transceiver.

11. A system comprising an external device and an associated implantable device, wherein the external device comprises:
    a device controller;
    a housing;
    an antenna array mounted to the housing;
    an RF transceiver operating at defined frequency, coupled to the antenna array;
    means for encoding signals to be transmitted to the implantable device, coupled to an input of the transceiver;
    means for decoding signals received from the implantable device, coupled to an output of the transceiver; and
    means for displaying the decoded signals received from the implantable device, mounted to the housing;
    wherein the antenna array comprises two antennas spaced a fraction of the wavelength of the defined frequency from one another, each antenna comprising two antenna elements mounted to the housing and located orthogonal to one another; and
    wherein the device controller includes means for selecting which of the two antennas is coupled to the transceiver; and
    wherein the implantable device comprises:
      a hermetic housing;
      a transceiver mounted within the hermetic housing;
      a first feedthrough, mounted to the housing and coupled to the transceiver; and
      an implantable antenna located external to the housing and coupled to the first feedthrough, the implantable antenna comprising a length of insulated conductor extending from the first feedthrough.

12. A system according to claim 11 wherein the implantable antenna comprises a metallic tab having first and second ends, the first end coupled to the first feedthrough an the second end coupled to the length of insulated conductor.

13. A system according to claim 12 wherein the implantable device comprises a non-conductive header mounted to the housing, wherein the metallic tab is mounted to the header.

14. A system according to claim 13 wherein the tab is mounted within the header.

15. A system according to claim 13 wherein the length of insulated conductor extends external to the header.

16. A device according to claim 12 wherein the tab is formed of a metal sheet and wherein the-second end of the tab has a width greater than the first end of the tab.

17. A system according to claim 12 wherein the implantable devices comprises a second feedthrough and wherein the header comprises means for connecting a medical electrical lead to the second feedthrough.

18. A system according to claim 11 wherein the implantable antenna comprises the length of conductor encased in a dielectric, extending from the first feedthrough, and a coaxial shield coupled to the housing and extending along only a portion of the length of conductor.

19. A system according to claim 18 comprising a non-conductive header mounted to the housing, wherein the coaxial shield is mounted to the header.

20. A device according to claim 19 wherein the coaxial shield is mounted within the header.

21. A system according to claim 18 wherein the implantable device comprises a second feedthrough and wherein the header comprises means for connecting a medical electrical lead to the second feedthrough.

22. A system according to any of claims 12 to 21 wherein the implantable transceiver is a UHF transceiver.

23. A system according to any of claims 12 to 21 wherein a portion of the external device housing is conductive and each external antenna comprises two tuned stub antenna elements having major axes orthogonal to one another, mounted to an extending from a conductive portion of the housing.

24. A system according to claim 23 wherein the major axis of each tuned stub element in one of the antennas is generally coplanar to the major axis of one of the stub elements in the other of the antennas.

25. A system according to claim 23 wherein the major axis of each tuned stub element in one of the antennas is generally parallel to the major axis of one of the stub elements in the other of the antennas.

26. A system according to claim 23 wherein the two antenna elements are coupled to one another by means of a 180 degree splitter.

27. A system according to any of claims 12 to 21 wherein a portion of the external housing is non-conductive and each external antenna comprises two generally planar conductive antenna elements mounted to a non-conductive portion of the housing and located generally along two mutually orthogonal planes.

28. A system according to claim 27 wherein the antenna elements are mounted along surfaces of the housing.

29. A system according to claim 28 wherein the antenna elements are metal strips or sheets adhered to surfaces of the housing.

30. A system according to any of claim 27 wherein the two antenna elements are coupled to one another by means of a 180 degree splitter.

* * * * *

UNITED STATES PATENT AND TRADEMARK OFFICE
CERTIFICATE OF CORRECTION

PATENT NO. : 6,169,925 B1
DATED : January 2, 2001
INVENTOR(S) : Villaseca et al.

It is certified that error appears in the above-identified patent and that said Letters Patent is hereby corrected as shown below:

<u>Title page,</u>
Item [57], Abstract,
Line 8, "housing and located oithogonal" should read -- housing and located orthogonal --

Signed and Sealed this

Thirtieth Day of October, 2001

Attest:

NICHOLAS P. GODICI
Attesting Officer
Acting Director of the United States Patent and Trademark Office